United States Patent [19]

Baumann et al.

[11] 4,081,482
[45] Mar. 28, 1978

[54] MANUFACTURE OF 2,6,6-TRIMETHYL-CYCLOHEX-2-EN-1-ONE

[75] Inventors: Manfred Baumann, Mannheim; Werner Hoffmann, Neuhofen, both of Germany

[73] Assignee: BASF Aktiengesellschaft, Ludwigshafen, Germany

[21] Appl. No.: 728,530

[22] Filed: Oct. 1, 1976

[30] Foreign Application Priority Data

Oct. 22, 1975 Germany .......................... 2547223

[51] Int. Cl.$^2$ .............................................. C07C 45/00
[52] U.S. Cl. ............................ 260/586 C; 260/593 R
[58] Field of Search ................................... 260/586 C

[56] References Cited

U.S. PATENT DOCUMENTS 3,692,839  9/1972  Wehrli .......................... 260/586 C

OTHER PUBLICATIONS

"Organic Reactions," vol. 16, pp. 2–11, (1968), John Wiley & Sons.
Heathcock et al., "Tetrahedron Letters," No. 52, pp. 4995–4996, (1971).
"Acrolein," C. W. Smith, Editor, Shell Development Co., (1962).
"Org. Reactions," Cope, Edit. in Chief, vol. 16, pp. 70–76, 94, 95, 178, 179, 192, 193, 198, 199, 202, 203, 238, 239, 242 and 243.

*Primary Examiner*—Norman Morgenstern
*Attorney, Agent, or Firm*—Keil, Thompson & Shurtleff

[57] ABSTRACT

2,6,6-Trimethyl-cyclohex-2-en-1-one is manufactured by reacting ethyl isopropyl ketone with acrolein in an organic solvent in the presence of a strong organic acid at from 40° to 150° C.

13 Claims, No Drawings

MANUFACTURE OF 2,6,6-TRIMETHYL-CYCLOHEX-2-EN-1-ONE

The present invention relates to a process for the manufacture of 2,6,6-trimethyl-cyclohex-2-en-1-one by reacting ethyl isopropyl ketone with acrolein in an organic solvent in the presence of a strong organic acid.

2,6,6,-Trimethyl-cyclohex-2-en-1-one is a valuable intermediate for numerous syntheses of scents. For example, damascenone, a highly desired scent, can be manufactured therefrom by a simple method entailing reaction with the lithium derivative of methyl ethynyl carbinol in liquid ammonia, followed by heating with formic acid (cf. S. Isoe et al., Helvetica Chimica Acta, 56, Fasc. 5(1973) No. 148, page 1,514). Furthermore, a number of important carotenoid syntheses are based on 2,6,6,-trimethyl-cyclohex-2-1-one, or on 2,6,6-trimethyl-cyclohexan-1-one obtainable therefrom by hydrogenation. Further details of how the ring components are built up in carotenoid syntheses may be found in O. Isler et al., Helv. Chim. Acta 39 (1956), 259 et seq.

Hitherto, only involved and expensive methods of manufacturing 2,6,6,-trimethyl-cyclohex-2-en-1-one have been available, for example by methylating 2-methylcyclohexanone with CH$_3$I/NaNH$_2$ or with dimethyl sulfate in anhydrous ether, purifying the resulting 2,6,6-trimethyl-cyclohexanone via the crystalline semicarbazone or by fractionation, then brominating the purified product with bromine in acetic acid and dehydrobrominating the product (cf. O. Isler: "Carotenoids", Birkhäuser Verlag, Basel and Stuttgart, 1971, pages 331–332).

German Published Application 1,668,874 discloses that ketones can be reacted with α,β-unsaturated carboxyl compounds in the presence of basic catalysts, to give cyclohexenones. Tetrahedron Letters 1971, 4995 discloses the reaction of an α,β-unsaturated carbonyl compound with a ketone to give a cyclohexenone, the starting materials being reacted by boiling in sulfuric acid, and the yield being about 50%. If this process is applied to ethyl isopropyl ketone and acrolein, 2,6,6-trimethyl-cyclohex-2-en-1-one is not obtained (see Comparative Example 9).

We have found, surprisingly, that 2,6,6-trimethyl-cyclohex-2-en-1-one can be manufactured particularly advantageously by reacting ethyl isopropyl ketone with acrolein in an organic solvent, in the presence of a strong organic acid as the catalyst, at from 40° to 150° C.

In the new process, the desired 2,6,6-trimethyl-cyclohex-2-en-1-one of the formula I is produced alongside the ketone of the formula II.

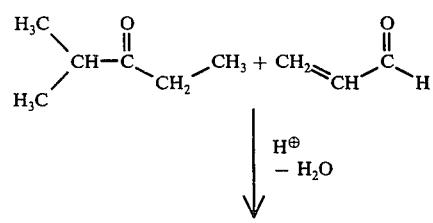

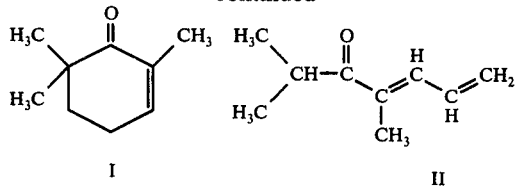

In the mixture of ketones I and II, formed in a yield of from 90 to 95%, the proportion of ketone I is from 70 to 80% by weight.

Organic solvents used are, for example, ethyl isopropyl ketone or solvents by means of which water can be removed azeotropically from the reaction mixtures, e.g. chloroform, methylene chloride, carbon tetrachloride, n-pentane, n-hexane, n-heptane, cyclohexane, benzene, xylene, chlorobenzene or toluene, amongst which those having a boiling point of from 70° to 120° C are preferred. If ethyl isopropyl ketone is used as the organic solvent, it is advantageous to employ an excess of from 2 to 10 moles of ethyl isopropyl ketone per mole of acrolein.

Strong organic acids which can be used are those having a pK$_a$ of <1, e.g. p-toluenesulfonic acid, benzenesulfonic acid, o-toluenesulfonic acid, p-methoxybenzenesulfonic acid, p-chlorobenzenesulfonic acid, p-bromo-benzenesulfonic acid, β-naphthylsulfonic acid, α-naphthylsulfonic acid and trichloroacetic acid, or strongly acid ion exchangers, i.e., ion exchangers containing SO$_3$H groups. p-Toluenesulfonic acid and benzenesulfonic acid are preferred. An advantageous amount of acid to use is from 0.01 to 0.1 mole per mole of acrolein.

The reaction is carried out at from 40° to 150° C, preferably at from 70° to 120° C. Preferably, at least 1 mole of ethyl isopropyl ketone, but especially from 1 to 5 moles of ethyl isopropyl ketone, is employed per mole of acrolein. The reactants are, for example, mixed and heated under reflux. However, it is also possible to add the acrolein dropwise to the boiling reaction mixture, and this gives somewhat better yields. It is also advantageous to distil the water of reaction from the reaction mixture during the reaction.

The reaction mixture may be worked up by, for example, distillation. The reaction product I which passes over at 75°–76° C/18 mm Hg contains at most 30% by weight of ketone II, and this proportion can decrease substantially if the reaction mixture is heated for fairly long periods. The relatively low proportion of compound II is surprising because the corresponding reaction of diethyl ketone with acrolein produces, virtually exclusively, the compound of the formula III which is analogous to the ketone II.

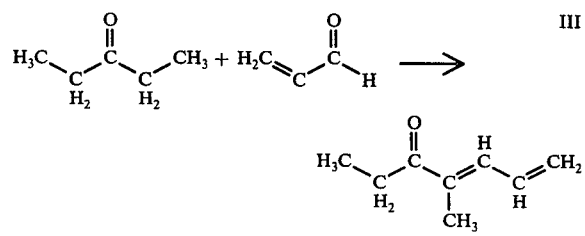

2,6,6-Trimethyl-cyclohex-2-en-1-one can be separated from compound II by various ways. For example, the mixture of I and II is heated, for example for from 0.5 to 10 hours, with or without solvent, and with or without the addition of catalytic amounts of acid, at from 150° to 250° C. This causes the polymerization of the compound II, whilst 2,6,6-trimethylcyclohex-2-en-1-one, which remains unchanged, is isolated in yields of from 65 to 75% by weight, based on the mixture of I and II, by distilling it at 75°–76° C/18 mm Hg.

The solvents which may be used for this working-up process are conventional organic solvents, e.g. ethers, hydrocarbons or chlorinated hydrocarbons.

An alternative method of isolating the 2,6,6-trimethylcyclohex-2-en-1-one is to distil the water of reaction, and the unconverted starting materials, from the reaction mixture obtained by reaction of ethyl isopropyl ketone with acrolein and subject the residue, in the same reaction vessel and before distilling off the 2,6,6-trimethylcyclohex-2-en-1-one, to the above treatment at from 150° to 250° C.

A further method of working up is, for example, to free the reaction mixture from unconverted starting materials and from water of reaction and treat it with hydrogen chloride at from 50° to 150° C. Since the compound I reacts much more slowly under these conditions than does the compound II, the desired product (I) can easily be isolated by distillation.

EXAMPLE 1

175 g of ethyl isopropyl ketone and 2 g, of p-toluenesulfonic acid are brought to the boil under a water separator. 30 g of acrolein are added dropwise in the course of about 60 minutes at a rate such that the boiling point does not fall below 103° C. When 7 ml of water have been removed, heating is discontinued (3.5 hours). The mixture is distilled first under atmospheric pressure and then under reduced pressure. 6 g of acrolein, 150 g of ethyl isopropyl ketone, 32 g of a mixture of compounds I and II (containing 27% of II) and 16 g of residue are obtained. This is equivalent to a yield of 93%, based on ethyl isopropyl ketone converted. The mixture of compounds I and II boils at 75°–76° C/18 mm Hg.

45 g of the resulting mixture of compounds I and II are heated for 3 hours at 200° C under nitrogen in a pressure apparatus. After cooling, the mixture is distilled under reduced pressure. At 75°–76° C/18 mm Hg, 30 g of pure 2,6,6-trimethyl-cyclohex-2-en-1-one are obtained. The yield is 67%, based on converted mixture of the compounds I and II.

EXAMPLE 2

The procedure followed is as described in Example 1, but 153 g of ethyl isopropyl ketone, 4 g of p-toluenesulfonic acid and 30 g of acrolein are employed. The acrolein is added dropwise in the course of 40 minutes. The reaction time is 75 minutes. The mixture of compounds I and II is obtained in a yield of 88%. It contains 23% by weight of II.

EXAMPLE 3

The procedure described in Example 1 is followed, but 149 g of ethyl isopropyl ketone, 1 g of p-toluenesulfonic acid and 30 g of acrolein are employed. The acrolein is added dropwise in the course of 2 hours. After 4 hours, 5 ml of water have been removed. The mixture of compounds I and II is obtained in a yield of 83%. It contains 30% by weight of compound II.

28 g of the resulting mixture are heated with 0.1 g of p-toluenesulfonic acid and 50 ml of hexane at 190° C for 4 hours. 18 g of pure 2,6,6-trimethylcyclohex-2-en-1-one are obtained at 75°–76° C/18 mm Hg. The yield is 64%, based on ethyl isopropyl ketone converted.

EXAMPLE 4

The procedure followed is as described in Example 1, but 130 g of ethyl isopropyl ketone and 2 g of benzenesulfonic acid are employed. 30 g of acrolein are added dropwise in the course of 40 minutes. 7 ml of water are removed in the course of 90 minutes. A mixture of the compounds I and II is obtained in a yield of 75%, based on ethyl isopropyl ketone converted, containing 77% I and 23% II.

EXAMPLE 5

30 g of acrolein are added dropwise in the course of 4 hours to 130 g of ethyl isopropyl ketone and 4 g of p-toluenesulfonic acid boiling under reflux, without using a water separator. The mixture is then boiled for a further hour under reflux. After it has cooled, 6 ml of water are separated off. Distillation gives 98 g of unconverted ethyl isopropyl ketone, 30 g of a mixture of compunds I and II, which however is not as pure as in the other examples (27% II) and 26 g of residue. The yield is 68%, based on ethyl isopropyl ketone converted.

EXAMPLE 6

30 g of acrolein are added dropwise in the course of 1 hour to 130 g of ethyl isopropyl ketone and 2 g of p-toluenesulfonic acid in 100 ml of chloroform under reflux. After 5 hours, 7 ml of water have been removed. The residue is distilled as described in Example 1. 103 g of unconverted ethyl isopropyl ketone, 25 g of a mixture of compounds I and II (30% II) and 25 g of residue are obtained. This amounts to a yield of 67%, based on ethyl isopropyl ketone converted.

EXAMPLE 7

30 g of acrolein (boiling point about 105° C) are added dropwise in the course of 60 minutes to 150 g of ethyl isopropyl ketone and 2 g of p-toluenesulfonic acid, under reflux. The water formed is removed. After 3 hours, the unconverted starting materials are distilled off through a short column under atmospheric pressure at from 40° to 112° C. The reaction mixture ist then kept for 1 hour at an internal temperature of 200° C and is thereafter distilled under reduced pressure. 7 g of water, 3 g of acrolein, 122 g of ethyl isopropyl ketone, 22 g of 2,6,6-trimethyl-cyclohex-2-en-1-one (free from isomers) and 28 g of residue are obtained. This amounts to a yield of 57%, based on ethyl isopropyl ketone employed.

EXAMPLE 8

A mixture of 100 g of ethyl isopropyl ketone, 2 g of trichloroacetic acid and 100 ml of cyclohexane is kept at the boil under reflux. 28 g of acrolein are added dropwise to the boiling mixture in the course of 3 hours and at the same time 9 ml of water are removed via a water separator. The residue is worked up as described in Example 1, giving 79 g of ethyl isopropyl ketone and 21 g of a mixture of compounds I and II. The yield is 72%, based on ethyl isopropyl ketone converted.

EXAMPLE 9 (COMPARATIVE EXAMPLE)

a. Procedure described in Tetrahedron Letters No. 52 (1971), pages 4,995–4,996

A mixture of 40 g (0.4 mole) of ethyl isopropyl ketone, 28 g (0.5 mole) of acrolein and 0.3 ml of $H_2SO_4$ is boiled under reflux for 16 hours.

The reaction mixture is cooled and 100 ml of hexane are added. After washing with 100 ml of 5% strength aqueous KOH, the solution is dried and concentrated. 35 g of a polymeric residue remain, from which it is not possible to obtain a defined product by distillation.

b. Alternative process variant, loc. cit.

A mixture of 40 g (0.4 mole) of ethyl isopropyl ketone, 28 g (0.5 mole) of acrolein and a solution of 0.3 ml of $H_2SO_4$ in 100 ml of water is boiled under reflux for 16 hours.

The reaction mixture is cooled and 100 ml of hexane are added. After washing with 100 ml of 5% strength aqueous KOH, the solution is dried and concentrated. 5.6 g of a residue which is essentially polymeric are obtained; whilst this material, according to IR spectroscopy, contains traces of a compound giving a carbonyl band, a defined product cannot be obtained from the residue by distillation.

We claim:

1. A process for the manufacture of 2,6,6-trimethyl-cyclohex-2-en-1-one which comprises reacting ethyl isopropyl ketone with acrolein in an organic solvent, at from 40° to 150° C. and in the presence of a strong organic acid as the catalyst which has a $pK_a$ of $>1$ and is selected from the group consisting of p-toluenesulfonic acid, benzenesulfonic acid, o-toluenesulfonic acid, p-methoxy-benzenesulfonic acid, p-chlorobenzenesulfonic acid, p-bromo-benzenesulfonic acid, β-naphthylsulfonic acid, α-naphthylsulfonic acid and trichloroacetic acid.

2. A process as claimed in claim 1, wherein ethyl isopropyl ketone is used as the organic solvent.

3. A process as claimed in claim 1, wherein the water formed during the reaction is distilled from the mixture during the reaction.

4. A process as claimed in claim 1, wherein the reaction mixture is subjected to distillation, the reaction product which distils off at 75°–76° C/18 mm Hg is heated at 150°–250° C, and 2,6,6-trimethyl-cyclohex-2-en-1-one is distilled from this product.

5. A process as claimed in claim 1, wherein the reaction mixture is freed from water of reaction and unconverted starting materials by distillation and then heated at 150°–250° C, after which 2,6,6-trimethyl-cyclohex-2-en-1-one is distilled off.

6. A process as claimed in claim 1, wherein the reaction mixture is freed from the water of reaction and unconverted starting materials by distillation and then treated with hydrogen chloride, after which 2,6,6-trimethyl-cyclohex-2-en-1-one is distilled off.

7. A process as claimed in claim 1, wherein the organic solvent can be azeotropically removed from the reaction mixture with water and has a boiling point of from 70° to 120° C.

8. A process as claimed in claim 1, wherein the organic solvent is selected from the group consisting of chloroform, methylene chloride, carbon tetrachloride, n-pentane, n-hexane, n-heptane, cyclohexane, benzene, xylene, chlorobenzene and toluene.

9. A process as claimed in claim 1, wherein the amount of strong organic acid used is from 0.01 to 0.1 mole per mole of acrolein.

10. A process as claimed in claim 1, wherein from 1 to 5 moles of ethyl isopropyl ketone is employed per mole of acrolein.

11. A process as claimed in claim 1, wherein the reaction of ethyl isopropyl ketone and acrolein produces a mixture of ketones of the formula I and II.

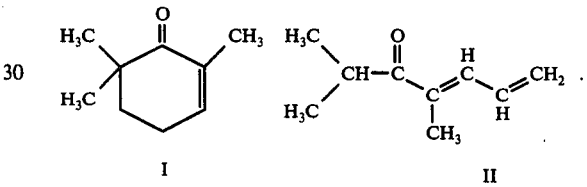

12. A process as claimed in claim 11, wherein the mixture of ketones I and II are formed in a yield of from 90 to 95% and the proportion of ketone I is from 70 to 80% by weight.

13. A process as claimed in claim 2, wherein the ethyl isopropyl ketone is used in an amount of from 2 to 10 moles per mole of acrolein.

* * * * *